United States Patent [19]

Sabbota

[11] 4,377,164
[45] Mar. 22, 1983

[54] SURGICAL VENTILATING APPARATUS

[75] Inventor: Howard I. Sabbota, Southfield, Mich.

[73] Assignee: Future Teck, Southfield, Mich.

[21] Appl. No.: 174,533

[22] Filed: Aug. 1, 1980

[51] Int. Cl.³ .................. A61M 15/08; A61M 25/00; B32B 9/00

[52] U.S. Cl. .................. 128/207.14; 128/348.1; 138/145; 165/180; 428/36; 428/376; 428/379; 428/389

[58] Field of Search ............... 128/207.14, 4, 10, 348, 128/349 R; 138/137, 143, 145; 165/180; 428/36, 376, 379, 384, 389, 469, 472, 398, 390

[56] References Cited

U.S. PATENT DOCUMENTS 2,707,691 5/1955 Wheildon, Jr. ............ 428/472
2,843,646 7/1958 Conant ................. 138/145 X
4,182,344 1/1980 Benson ................... 428/36

FOREIGN PATENT DOCUMENTS 55-17577 5/1980 Japan .................. 128/4

Primary Examiner—Lorraine T. Kendell
Attorney, Agent, or Firm—Basile, Weintraub & Hanlon

[57] ABSTRACT

Surgical ventilating apparatus for use in laser surgical techniques. The surgical ventilating apparatus comprises a tubular body having an inner, hollow, flexible metallic member and an outer layer formed of a heat-resistant material. Preferably, the inner member is formed of molybdenum and the outer layer is formed of a heat resistant coating, such as an oxide of a metal, an expanded or foamed silica or quartz, and the like. A connector adapted to be connected to one end of the tubular body enables the tubular body to be connected to ventilating equipment for controlling the respiration of the patient during surgery.

5 Claims, 3 Drawing Figures

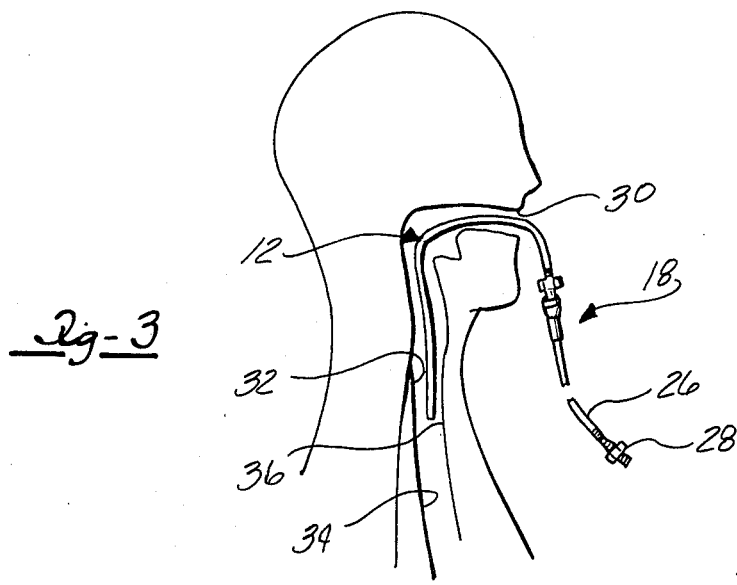
_Fig-3_
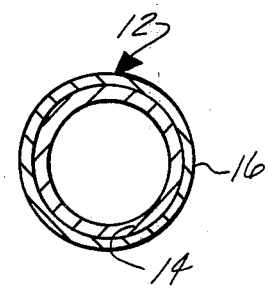
_Fig-2_
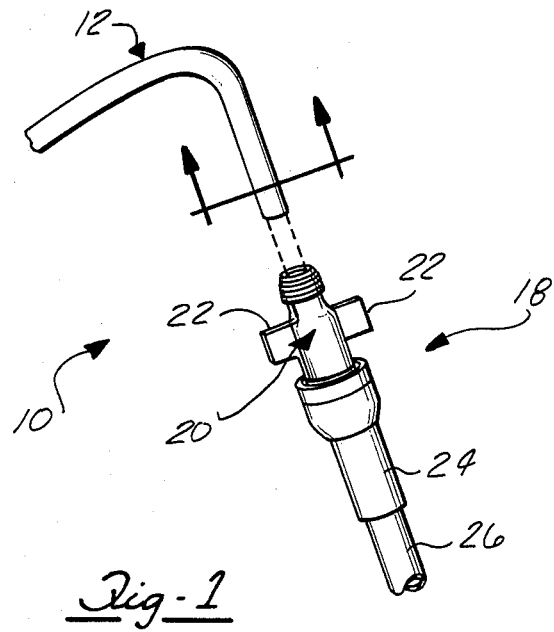
_Fig-1_

SURGICAL VENTILATING APPARATUS

BACKGROUND OF THE INVENTION

1. Field of the Invention

This invention relates, in general, to surgical apparatus and, more specifically, to surgical ventilating apparatus, such as tracheal tubes.

2. Description of the Prior Art

A commonly used device in the medical field is a tracheal tube which is particularly useful during surgical procedures for maintaining control over the patient's breathing. Commonly, tracheal tubes are manufactured from resilient type materials which automatically conform in shape and curvature to the body requirements.

As is well known, present day tracheal tubes are inserted through the patient's mouth and beyond, into the lower portions of the trachea. The outer end of the tube is connected to suitable medical apparatus, such as a suction device for aspirating the trachea, a source of anesthesia or the like.

Although such tracheal tubes function effectively to permit controlled respiration of the patient, recent surgical advances, such as microlaryngeal operations utilizing lasers, have posed problems for their continued effective use. In such laser surgical techniques, the heat generated by the high intensity laser beams quickly perforates or severs conventionally constructed tracheal tubes, rendering them useless and posing serious danger to the patient.

Efforts to construct tracheal tubes of material having a higher heat resistivity have met with little success. Tubes covered with aluminum foil tape and/or muslin wrappings present the danger of small portions becoming dislodged during surgery as well as being relatively complex and cumbersome to construct.

Further, most material having the necessary high heat resistivity is somewhat rigid which retards its safe use during insertion and removal from the patient's trachea.

Thus, it would be desirable to provide a surgical ventilating apparatus which overcomes the problems of the prior art ventilating apparatus when used in surgical techniques using lasers, as well as bronchoscopy, or endoscopy techniques. It would also be desirable to provide a surgical ventilating apparatus which minimizes the danger to the patient during its use. It would also be desirable to provide a surgical ventilating apparatus which is simple to construct and which resists high intensity laser beams. Finally, it would be desirable to provide a surgical ventilating apparatus which is flexible so as to conform in shape and curvature to the patient's trachea.

SUMMARY OF THE INVENTION

There is disclosed herein a new and improved surgical ventilating apparatus useful in surgical procedures which must provide greater access to the tracheal area. The present invention is particularly useful with surgical techniques utilizing high intensity lasers, bronchoscopies or endoscopies. The surgical ventilating apparatus of this invention comprises a tubular body having an inner, hollow, flexible metallic member. An outer layer formed of a heat-resistant material surrounds the inner metallic member. Preferably, the inner member is formed of molybdenum and the outer layer is formed of an oxide, such as an aluminum oxide or a blend thereof with magnesium oxide, silver oxide, and the like. Other useful materials include expanded or foamed silica, perlite and quartz. Suitable connector means adapted to be secured to one end of the tubular body enable the surgical ventilating apparatus of this invention to be connected to conventional ventilating equipment for controlling the respiration of the patient.

The new and improved surgical ventilating apparatus of this invention is ideally suited for use with newly developed surgical techniques utilizing high intensity laser beams for cutting or cauterizing. The tubular body is flexible so as to conform in shape and curvature to the body requirements of the patient's trachea. Further, the heat resistive outer layer resists the high intensity heat beams generated by the laser which heretofore frequently perforate or sever conventionally formed tracheal tubes. Finally, the surgical ventilating apparatus of this invention is simple to construct which further enhances its use in those surgical techniques requiring greater access to the tracheal area.

BRIEF DESCRIPTION OF THE DRAWING

The various features, advantages and other uses of this invention will become more apparent by referring to the following detailed description and drawing in which:

FIG. 1 is a perspective view of a surgical ventilating apparatus constructed in accordance with the teachings of this invention;

FIG. 2 is a cross sectional view, generally taken along line 2—2 in FIG. 1, showing the construction of the surgical ventilating apparatus of this invention; and FIG. 3 is a schematic view of the surgical ventilating apparatus of the present invention into the trachea of the patient.

DESCRIPTION OF THE PREFERRED EMBODIMENTS

Throughout the following description and drawing, identical reference numbers are used to refer to the same component shown in multiple figures of the drawing.

Referring now to the drawing, and to FIG. 1 in particular, there is illustrated a surgical ventilating apparatus 10 constructed in accordance with the teachings of the present invention. The surgical ventilating apparatus 10 is constructed so as to be suitable for use with surgical tchniques utilizing high intensity laser beams.

The surgical ventilating apparatus 10 of this invention comprises an elongated tubular body 12. The tubular body 12 may be of any suitable length, such as 11 to 12 inches, and may further be constructed of varying diameters so as to be utilized in many different surgical applications and with different sized patients, from babies to adults.

As shown in FIG. 2, the tubular body 12 is constructed of an inner member 14. The inner member 14 is of substantially circular cross section and forms a hollow conduit throughout the length of the tubular body 12. The inner member 14 is constructed of a suitable metallic material which is flexible so as to conform to the shape and curvature of the trachea of a patient. Preferably, the inner member 14 is formed of molybdenum.

The tubular body 12 also includes an outer layer 16 which is formed of a material having high heat resistivity so as to resist deterioration or perforation under the bombardment of high intensity laser beams during surgery. The outer layer 16 completely surrounds the outer surface of the inner member 14 and is joined thereto in secure engagement by any conventional joining means, such as by molding, coating of otherwise depositing the outer layer 16 around the inner member 14. Preferably, the outer layer 16 is formed of any non-toxic material which can withstand the high temperatures generated during laser base surgery. Particularly useful are certain oxide coatings which can be deposited onto the flexible tube by any conventional technique. Suitable oxides include, for example, aluminum oxide, magnesium oxide, as well as blends thereof, silver oxide, zinc oxide, titanium oxide and the like. Other useful materials include expanded or foamed silica, foamed quartz and expanded perlite. Depending on the temperature, aluminates may be used. In practicing the present invention, the outer layer is, preferably, either aluminum oxide or a blend thereof with magnesium oxide, such as that sold under the name Fiberflex. Mixtures of the materials can be used.

Referring again to FIGS. 1 and 3, the surgical ventilating apparatus 10 of this invention includes means, denoted in general at reference number 18, for connecting the surgical ventilating apparatus 10 to conventionally formed ventilating equipment, such as a suction device for aspirating the trachea or a source of anesthesia, not shown. The connecting means 18 includes a suitably formed hollow connector 20 having a plurality of threads extending from opposed sides thereof. The connector 20 includes a pair of flanges 22 which form a convenient means for screwing the connector 20 into one end of the tubular body 12. The opposite end of the connector 20 is threadingly secured to a sleeve 24 which sealingly mates a hollow conduit 26, such as plastic tubing, to the connector 20. As shown in FIG. 3, the opposite end of the conduit 26 is provided with a suitably formed connector 28 so as to enable the conduit 26 to be joined to the desired ventilating equipment.

In use, the connector 20 is threadingly secured to one end of the tubular body 12. The conduit 26 is then joined to the opposite end of the connector 20, with the opposed end of the conduit 26 joined to the ventilating equipment by means of the connector 28.

As shown in FIG. 3, the first portion of the tubular body 12 is inserted through the mouth 30 and larnyx 32 of a patient. The tubular body 12 is inserted into the trachea 34 of the patient until the end thereof is properly positioned in the vestibular portion 36 of the trachea 34 of the patient. In this manner, controlled respiration of the patient during surgery can be easily obtained. In addition, surgical equipment incorporating high intensity lasers may then be inserted and directed into the trachea 34 of the patient without danger of the heat generated by the high intensity laser beams perforating or severing the tubular body 12 and posing a danger to the patient. It should be noted with respect hereto that the connector assembly hereof is useful with any conventional anesthesia breathing circuit, such as a Sanders ventilator or the like.

Thus, there has been described herein a new and improved surgical ventilating apparatus that is suitable for use with new surgical techniques utilizing high intensity lasers, bronchoscopies, endoscopies and the like which require greater access to the tracheal area. The surgical ventilating apparatus comprises a tubular body adapted to be inserted into the trachea of the patient which is constructed of an inner hollow metallic member and an outer coating of a heat-resistive material. The heat-resistive material resists perforation despite bombardment of the heat generated by the high intensity laser during surgical procedures. In this manner, respiration of the patient during surgery is continually controlled with little additional danger posed to the patient by the use of the high intensity laser.

What is claimed is:

1. In laser-based surgical ventilating apparatus of the type comprising a tracheal tube insertable into the throat of a surgery patient and ventilating equipment connected to the tube at one end thereof, the improvement which comprises:
a tracheal tube comprising:
  (a) a hollow, flexible metallic member, and
  (b) an outer layer heat bonded onto the metallic member, the outer layer being resistant to perforation by the heat generated during laser surgery and being of a material selected from the group comprising aluminum oxide, magnesium oxide and blends thereof, silver oxide, zinc oxide, titanium oxide, expanded silica, expanded perlite, foamed quartz, an aluminate or mixtures thereof.

2. The surgical ventilating apparatus of claim 1 wherein the inner member is formed of molybdenum.

3. The surgical apparatus of claim 1 wherein the outer layer is aluminum oxide.

4. The surgical apparatus of claim 1 wherein the outer layer is a blend of aluminum oxide and magnesium oxide.

5. The surgical apparatus of claim 1 wherein:
the inner member is formed of molybdenum; and
the outer layer is formed of a material selected from the group consisting of aluminum oxide, magnesium oxide and blends thereof, silver oxide, zinc oxide, titanium oxide, expanded silica, expanded perlite, foamed quartz, and aluminate or mixtures thereof.

* * * * *